United States Patent
Tran et al.

(10) Patent No.: US 8,369,960 B2
(45) Date of Patent: Feb. 5, 2013

(54) SYSTEMS AND METHODS FOR CONTROLLING WIRELESS SIGNAL TRANSFERS BETWEEN ULTRASOUND-ENABLED MEDICAL DEVICES

(75) Inventors: Binh C. Tran, Minneapolis, MN (US); Bin Mi, Plymouth, MN (US); Robert S. Harguth, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 863 days.

(21) Appl. No.: 12/367,337

(22) Filed: Feb. 6, 2009

(65) Prior Publication Data

US 2009/0201148 A1 Aug. 13, 2009

Related U.S. Application Data

(60) Provisional application No. 61/027,983, filed on Feb. 12, 2008.

(51) Int. Cl.
*A61N 1/00* (2006.01)
(52) U.S. Cl. ............ 607/60; 207/30; 207/31; 207/32; 207/59
(58) Field of Classification Search ........... 607/30–32, 607/59, 60
See application file for complete search history.

(56) References Cited

U.S. PATENT DOCUMENTS

| | | | |
|---|---|---|---|
| 3,310,885 A | 3/1967 | Alderson | |
| 3,320,946 A | 5/1967 | Dethloff et al. | |
| 3,536,836 A | 10/1970 | Pfeiffer | |
| 3,568,661 A | 3/1971 | Franklin | |
| 3,672,352 A | 6/1972 | Summers | |
| 3,692,027 A | 9/1972 | Ellinwood | |
| 3,757,770 A | 9/1973 | Brayshaw et al. | |
| 3,794,840 A | 2/1974 | Scott | |
| 3,943,915 A | 3/1976 | Severson | |
| 4,003,379 A | 1/1977 | Ellinwood | |
| 4,041,954 A | 8/1977 | Ohara | |
| 4,127,110 A | 11/1978 | Bullara | |
| 4,146,029 A | 3/1979 | Ellinwood | |
| 4,223,801 A | 9/1980 | Carlson | |
| 4,227,407 A | 10/1980 | Drost | |
| 4,237,900 A | 12/1980 | Schulman et al. | |
| 4,281,664 A | 8/1981 | Duggan | |

(Continued)

FOREIGN PATENT DOCUMENTS

| EP | 0897690 | 2/1999 |
|---|---|---|
| EP | 0928598 | 7/1999 |

(Continued)

OTHER PUBLICATIONS

Bourgeois, Maurice J. et al., "Continuous Determination of Beat-to-Beat Stroke vol. from Aortic pressure Pulses in the Dog", Circulation Research, vol. 39, pp. 15-24 (1976).

(Continued)

*Primary Examiner* — Niketa I. Patel
*Assistant Examiner* — Lindsey G Hankins
(74) *Attorney, Agent, or Firm* — Faegre Baker Daniels LLP (57) ABSTRACT

Systems and methods for wireless signal transfers between ultrasound-enabled medical devices are disclosed. An illustrative system includes a source device equipped with multiple transducer elements configured to transmit an acoustic wave, a target device including an acoustic transducer for receiving the acoustic wave from the source device, and a controller configured to determine adjustments to one or more transmission parameters of the source device for increasing the signal coherence of the acoustic wave at the target device.

19 Claims, 8 Drawing Sheets

U.S. PATENT DOCUMENTS

| | | |
|---|---|---|
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,719,921 A | 1/1988 | Chirife |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Benjamin et al. |
| 4,809,697 A | 3/1989 | Causey, III et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,003,976 A | 4/1991 | Alt |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,113,859 A | 5/1992 | Funke |
| 5,139,020 A | 8/1992 | Koestner et al. |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A | 2/1993 | Kraidin et al. |
| 5,188,106 A | 2/1993 | Nappholz et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,246,008 A | 9/1993 | Mueller |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,314,457 A | 5/1994 | Jeutter et al. |
| 5,329,459 A | 7/1994 | Kaufman et al. |
| 5,330,505 A | 7/1994 | Cohen |
| 5,339,051 A | 8/1994 | Koehler et al. |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,445,608 A | 8/1995 | Chen et al. |
| 5,454,838 A | 10/1995 | Vallana et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,509,424 A | 4/1996 | Al-Ali |
| 5,528,067 A | 6/1996 | Farb |
| 5,535,752 A | 7/1996 | Halperin et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,604,531 A | 2/1997 | Iddan et al. |
| 5,605,154 A * | 2/1997 | Ries et al. .................. 600/444 |
| 5,619,997 A | 4/1997 | Kaplan |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,728,281 A | 3/1998 | Holmstrom et al. |
| 5,729,129 A | 3/1998 | Acker |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,776,324 A | 7/1998 | Usala |
| 5,792,195 A | 8/1998 | Carlson et al. |
| 5,796,827 A | 8/1998 | Coppersmith et al. |
| 5,797,395 A | 8/1998 | Martin |
| 5,800,478 A | 9/1998 | Chen et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,832,924 A | 11/1998 | Archibald et al. |
| 5,833,603 A | 11/1998 | Kovacs et al. |
| 5,835,455 A | 11/1998 | Hanson et al. |
| 5,836,300 A | 11/1998 | Mault |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,886,267 A | 3/1999 | Ortiz |
| 5,891,180 A | 4/1999 | Greeninger et al. |
| 5,904,708 A | 5/1999 | Goedeke |
| 5,911,685 A | 6/1999 | Siess et al. |
| 5,919,221 A | 7/1999 | Miesel |
| 5,941,249 A | 8/1999 | Maynard |
| 5,954,641 A | 9/1999 | Kehr et al. |
| 5,957,950 A | 9/1999 | Mockros et al. |
| 5,967,986 A | 10/1999 | Cimochowski et al. |
| 5,979,898 A | 11/1999 | Pan |
| 6,002,963 A | 12/1999 | Mouchawar et al. |
| 6,023,641 A | 2/2000 | Thompson |
| 6,024,704 A | 2/2000 | Meador et al. |
| 6,050,951 A | 4/2000 | Friedman et al. |
| 6,053,873 A | 4/2000 | Govari et al. |
| 6,083,248 A | 7/2000 | Thompson |
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A | 10/2000 | Cox et al. |
| 6,152,885 A | 11/2000 | Taepke |
| 6,155,267 A | 12/2000 | Nelson |
| 6,161,032 A | 12/2000 | Acker |
| 6,162,238 A | 12/2000 | Kaplan et al. |

| Patent No. | Date | Inventor |
|---|---|---|
| 6,171,252 B1 | 1/2001 | Roberts |
| 6,179,767 B1 | 1/2001 | Ziegler et al. |
| 6,185,452 B1 | 2/2001 | Schulman et al. |
| 6,198,965 B1 | 3/2001 | Penner et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,237,398 B1 | 5/2001 | Porat et al. |
| 6,239,724 B1 | 5/2001 | Doron et al. |
| 6,248,080 B1 | 6/2001 | Miesel et al. |
| 6,256,538 B1 | 7/2001 | Ekwall |
| 6,266,567 B1 | 7/2001 | Ishikawa et al. |
| 6,273,904 B1 | 8/2001 | Chen et al. |
| 6,277,078 B1 | 8/2001 | Porat et al. |
| 6,278,894 B1 | 8/2001 | Salo et al. |
| 6,298,267 B1 | 10/2001 | Rosborough et al. |
| 6,305,381 B1 | 10/2001 | Weijand et al. |
| 6,308,099 B1 | 10/2001 | Fox et al. |
| 6,314,323 B1 | 11/2001 | Ekwall |
| 6,330,957 B1 | 12/2001 | Bell-Greenstreet |
| 6,331,163 B1 | 12/2001 | Kaplan |
| 6,368,275 B1 | 4/2002 | Sliwa et al. |
| 6,397,661 B1 | 6/2002 | Grimes et al. |
| 6,409,674 B1 | 6/2002 | Brockway et al. |
| 6,409,675 B1 | 6/2002 | Turcott |
| 6,411,850 B1 | 6/2002 | Kay et al. |
| 6,416,474 B1 | 7/2002 | Penner et al. |
| 6,421,565 B1 | 7/2002 | Hemmingsson |
| 6,431,175 B1 | 8/2002 | Penner et al. |
| 6,432,050 B1 | 8/2002 | Porat et al. |
| 6,438,408 B1 | 8/2002 | Mulligan et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,883 B1 | 9/2002 | Torgerson et al. |
| 6,471,645 B1 | 10/2002 | Warkentin et al. |
| 6,472,991 B1 | 10/2002 | Schulman et al. |
| 6,475,147 B1 | 11/2002 | Yost et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,522,914 B1 | 2/2003 | Huvelle et al. |
| 6,567,700 B1 | 5/2003 | Turcott et al. |
| 6,574,510 B2 | 6/2003 | Von Arx et al. |
| 6,580,946 B2 | 6/2003 | Struble |
| 6,604,000 B2 | 8/2003 | Lu |
| 6,607,485 B2 | 8/2003 | Bardy |
| 6,609,023 B1 | 8/2003 | Fischell et al. |
| 6,615,083 B2 | 9/2003 | Kupper |
| 6,622,049 B2 | 9/2003 | Penner et al. |
| 6,628,989 B1 | 9/2003 | Penner et al. |
| 6,638,231 B2 | 10/2003 | Govari et al. |
| 6,644,322 B2 | 11/2003 | Webb |
| 6,654,638 B1 | 11/2003 | Sweeney |
| 6,675,049 B2 | 1/2004 | Thompson et al. |
| 6,699,186 B1 | 3/2004 | Wolinsky et al. |
| 6,702,847 B2 | 3/2004 | DiCarlo |
| 6,708,061 B2 | 3/2004 | Salo et al. |
| 6,708,065 B2 | 3/2004 | Von Arx et al. |
| 6,712,772 B2 | 3/2004 | Cohen et al. |
| 6,720,709 B2 | 4/2004 | Porat et al. |
| 6,720,887 B1 | 4/2004 | Zunti |
| 6,733,447 B2 | 5/2004 | Lai et al. |
| 6,738,667 B2 | 5/2004 | Deno et al. |
| 6,738,671 B2 | 5/2004 | Christophersom et al. |
| 6,743,173 B2 | 6/2004 | Penner et al. |
| 6,758,822 B2 | 7/2004 | Romano |
| 6,764,446 B2 | 7/2004 | Wolinsky et al. |
| 6,782,810 B2 | 8/2004 | Vilo |
| 6,783,499 B2 | 8/2004 | Schwartz |
| 6,792,308 B2 | 9/2004 | Corbucci |
| 6,792,311 B2 | 9/2004 | Fox et al. |
| 6,805,667 B2 | 10/2004 | Christopherson et al. |
| 6,809,507 B2 | 10/2004 | Morgan et al. |
| 6,824,512 B2 | 11/2004 | Warkentin et al. |
| 6,832,112 B1 | 12/2004 | Bornzin |
| 6,840,956 B1 | 1/2005 | Wolinsky et al. |
| 6,855,115 B2 | 2/2005 | Fonseca et al. |
| 6,859,665 B2 | 2/2005 | Ding et al. |
| 6,865,419 B2 | 3/2005 | Mulligan et al. |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,889,086 B2 | 5/2005 | Mass et al. |
| 6,895,265 B2 | 5/2005 | Silver |
| 6,907,285 B2 | 6/2005 | Denker et al. |
| 6,915,162 B2 | 7/2005 | Noren et al. |
| 6,926,670 B2 | 8/2005 | Rich et al. |
| 6,937,900 B1 | 8/2005 | Pianca et al. |
| 6,949,075 B2 | 9/2005 | Hatlesad et al. |
| 6,961,448 B2 | 11/2005 | Nichols et al. |
| 6,970,742 B2 | 11/2005 | Mann et al. |
| 6,978,182 B2 | 12/2005 | Mazar et al. |
| 6,985,773 B2 | 1/2006 | Von Arx et al. |
| 6,993,393 B2 | 1/2006 | Von Arx et al. |
| 7,003,350 B2 | 2/2006 | Denker et al. |
| 7,018,336 B2 | 3/2006 | Enegren et al. |
| 7,024,248 B2 | 4/2006 | Penner et al. |
| 7,033,322 B2 | 4/2006 | Silver |
| 7,035,684 B2 | 4/2006 | Lee |
| 7,047,065 B2 | 5/2006 | Kalgren et al. |
| 7,048,691 B2 | 5/2006 | Miele et al. |
| 7,060,030 B2 | 6/2006 | Von Arx et al. |
| 7,061,381 B2 | 6/2006 | Forcier et al. |
| 7,088,254 B2 | 8/2006 | Liebenow |
| 7,127,290 B2 | 10/2006 | Girouard et al. |
| 7,130,681 B2 | 10/2006 | Gebhardt et al. |
| 7,134,999 B2 | 11/2006 | Brauker et al. |
| 7,136,703 B1 | 11/2006 | Cappa et al. |
| 7,160,252 B2 | 1/2007 | Cho et al. |
| 7,181,268 B2 | 2/2007 | Sheldon et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,203,545 B2 | 4/2007 | Schmitt et al. |
| 7,204,798 B2 | 4/2007 | Zdeblick et al. |
| 7,209,790 B2 | 4/2007 | Thompson et al. |
| 7,212,861 B1 | 5/2007 | Park et al |
| 7,214,189 B2 | 5/2007 | Zdeblick |
| 7,236,821 B2 | 6/2007 | Cates et al. |
| 7,248,923 B2 | 7/2007 | Maile et al. |
| 7,273,457 B2 | 9/2007 | Penner |
| 7,294,105 B1 | 11/2007 | Islam |
| 7,335,161 B2 | 2/2008 | Von Arx et al. |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 7,742,815 B2 | 6/2010 | Salo et al. |
| 2001/0051766 A1 | 12/2001 | Gazdzinski |
| 2001/0051787 A1 | 12/2001 | Haller et al. |
| 2002/0022785 A1 | 2/2002 | Romano |
| 2002/0023123 A1 | 2/2002 | Madison |
| 2002/0042561 A1 | 4/2002 | Schulman et al. |
| 2002/0045812 A1 | 4/2002 | Ben-Haim et al. |
| 2002/0045836 A1 | 4/2002 | Alkawwas |
| 2002/0062086 A1 | 5/2002 | Miele et al. |
| 2002/0120204 A1 | 8/2002 | Pfeiffer et al. |
| 2002/0126036 A1 | 9/2002 | Flaherty et al. |
| 2002/0147406 A1 | 10/2002 | von Segesser |
| 2002/0151770 A1 | 10/2002 | Noll, III et al. |
| 2002/0183628 A1 | 12/2002 | Reich et al. |
| 2002/0188323 A1 | 12/2002 | Penner et al. |
| 2003/0009204 A1 | 1/2003 | Amundson et al. |
| 2003/0045805 A1 | 3/2003 | Sheldon et al. |
| 2003/0060723 A1 | 3/2003 | Joo et al. |
| 2003/0114897 A1 | 6/2003 | Von Arx et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0199779 A1 | 10/2003 | Muhlenberg et al. |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |

| | | | |
|---|---|---|---|
| 2004/0152999 A1 | 8/2004 | Cohen et al. | |
| 2004/0158163 A1 | 8/2004 | Cohen et al. | |
| 2004/0167416 A1 | 8/2004 | Lee | |
| 2004/0172081 A1 | 9/2004 | Wang | |
| 2005/0056539 A1 | 3/2005 | Morgan et al. | |
| 2005/0102002 A1 | 5/2005 | Salo et al. | |
| 2005/0109339 A1 | 5/2005 | Stahmann et al. | |
| 2005/0124904 A1 | 6/2005 | Roteliuk | |
| 2005/0137490 A1 | 6/2005 | Scheiner et al. | |
| 2005/0149143 A1 | 7/2005 | Libbus et al. | |
| 2005/0154321 A1 | 7/2005 | Wolinsky et al. | |
| 2005/0159639 A1 | 7/2005 | Skliar et al. | |
| 2005/0159789 A1 | 7/2005 | Brockway et al. | |
| 2005/0182330 A1 | 8/2005 | Brockway et al. | |
| 2005/0187482 A1 | 8/2005 | O'Brien et al. | |
| 2005/0192637 A1 | 9/2005 | Girouard et al. | |
| 2005/0192844 A1 | 9/2005 | Esler et al. | |
| 2005/0197585 A1 | 9/2005 | Brockway et al. | |
| 2005/0215887 A1 | 9/2005 | Ben-Haim et al. | |
| 2005/0242479 A1 | 11/2005 | Petisce et al. | |
| 2005/0267379 A1 | 12/2005 | Pfeiffer et al. | |
| 2005/0288727 A1 | 12/2005 | Penner | |
| 2006/0009818 A1* | 1/2006 | Von Arx et al. | 607/60 |
| 2006/0031378 A1 | 2/2006 | Vallapureddy et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0089694 A1 | 4/2006 | Zhang et al. | |
| 2006/0122522 A1 | 6/2006 | Chavan et al. | |
| 2006/0136004 A1 | 6/2006 | Cowan et al. | |
| 2006/0142651 A1 | 6/2006 | Brister et al. | |
| 2006/0167359 A1 | 7/2006 | Bennett et al. | |
| 2006/0235323 A1 | 10/2006 | Hatib et al. | |
| 2007/0043394 A1 | 2/2007 | Zhang et al. | |
| 2007/0049977 A1 | 3/2007 | Von Arx et al. | |
| 2007/0060959 A1 | 3/2007 | Salo et al. | |
| 2007/0129765 A1 | 6/2007 | Gilkerson et al. | |
| 2007/0142727 A1 | 6/2007 | Zhang et al. | |
| 2007/0142866 A1 | 6/2007 | Li et al. | |
| 2007/0149890 A1 | 6/2007 | Li et al. | |
| 2007/0161914 A1 | 7/2007 | Zdeblick et al. | |
| 2007/0197921 A1 | 8/2007 | Cohen et al. | |
| 2007/0282210 A1 | 12/2007 | Stern | |
| 2007/0282381 A1 | 12/2007 | Li et al. | |
| 2008/0015421 A1 | 1/2008 | Penner | |
| 2008/0015651 A1 | 1/2008 | Ettori et al. | |
| 2008/0021333 A1 | 1/2008 | Huelskamp | |
| 2008/0021972 A1 | 1/2008 | Huelskamp et al. | |
| 2008/0046037 A1 | 2/2008 | Haubrich et al. | |
| 2008/0051843 A1 | 2/2008 | Li et al. | |
| 2008/0071178 A1 | 3/2008 | Greenland et al. | |
| 2008/0077440 A1 | 3/2008 | Doron | |
| 2009/0204163 A1 | 8/2009 | Shuros et al. | |
| 2009/0228078 A1 | 9/2009 | Zhang et al. | |
| 2010/0056931 A1 | 3/2010 | Soffer et al. | |
| 2010/0094144 A1 | 4/2010 | Doron | |
| 2010/0125211 A1 | 5/2010 | Stahmann et al. | |
| 2010/0222833 A1 | 9/2010 | Salo et al. | |
| 2010/0324378 A1 | 12/2010 | Tran et al. | |

FOREIGN PATENT DOCUMENTS

| | | |
|---|---|---|
| EP | 1266606 | 12/2002 |
| EP | 1169085 | 8/2004 |
| JP | 03-034196 | 2/1991 |
| JP | 10-055202 | 2/1998 |
| JP | 2004528152 | 9/2004 |
| JP | 2006-523120 | 10/2006 |
| JP | 2007-519441 | 7/2007 |
| WO | WO83/03345 | 10/1983 |
| WO | WO95/03086 | 2/1995 |
| WO | WO95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO 01/85094 | 11/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO2004012808 | 2/2004 |
| WO | WO 2004/091719 | 10/2004 |
| WO | WO2005000206 | 1/2005 |
| WO | WO 2005/063332 | 7/2005 |
| WO | WO2005/089638 | 9/2005 |
| WO | WO2005/118056 | 12/2005 |
| WO | WO2006/033812 | 3/2006 |
| WO | WO2006/034183 | 3/2006 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO2007/030474 | 3/2007 |
| WO | WO2007/047287 | 4/2007 |
| WO | WO2007/070794 | 6/2007 |
| WO | WO2007/099533 | 9/2007 |
| WO | WO 2008/011570 | 1/2008 |
| WO | WO2008/011592 | 1/2008 |
| WO | WO2008/011593 | 1/2008 |
| WO | WO2008/154145 | 12/2008 |

OTHER PUBLICATIONS

Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.

Wesseling, KH et al., "Computation of Aortic Flow From Pressure in Humans Using a Nonlinear, Three-Element Model", Journal of Applied Physiology, vol. 74, Issue 5, pp. 2566-2573 (1993).

B. C. Penney et al., "Simplified electrode array for impedance cardiography," Medical & Biological Engineering & Computing, 1985, 23, p. 1-7.

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

C. Hierold et al. (Germany, 1998) "Implantable Low Power Integrated Pressure Sensor System for Minimal Invasive Telemetric Patient Monitoring" IEEE, pp. 568-573.

Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech 1993, Jan 26: 19-35.

Hetzer R. et al., 1998, Daily non-invasive rejection monitoring improves long-term survival in pediatric heart transplantation, Ann. Thorac. Surg. (66):1343-1349.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodoflurescin Isothiocyanate Dextran. A strategy for the isolation of Thermoconditional Endocytosis Mutants," published in Photochemistry and Photobiology, 1993, vol. 67, No. 3, pp. 531-537.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem for Biomedical Applications" Micro System Technologies 96, pp. 717-722.

S.K. Gupta et al. (1999) "Use of a Piezoelectric Film Sensor for Monitoring Vascular Grafts", The American Journal of Surgery, vol. 160, pp. 182-186.

T. Chuter et al. (Sweden, Jan. 1997) "Aneurysm Pressure Following Endovascular Exclusion" Eur. J. Vasc. Endovasc. Surg. vol. 13, pp. 85-87.

T.A. Cochran et al. (1990) "Aortic Aneurysm Abdominal", Current Therapy in Adult Medicine, Fourth Edition.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Cohen, T.J. et al., "A Hemodynamically Responsive Antitachycardia System. Development and Basis for Design in Humans", Circulation 1990, vol. 82, No. 2, pp. 394-406, XP002560584.

Blacher, Jacques et al., "Aortic Pulse Wave Velocity as a Member of Cardiovascular Risk in Hypertensive Patients", Hypertension May 1999;33;1111-1117.

Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.

El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.

Fujiki, Akira et al., "Pacemaker Syndrome Evaluated by Cardiopulmonary Exercise Testing", PACE, vol. 13, Oct. 1990, pp. 1236-1241.

International Search Report and Written Opinion issued in PCT/US2009/033436, mailed May 27, 2009, 12 pages.

Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.

Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.

Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.

* cited by examiner

SYSTEMS AND METHODS FOR CONTROLLING WIRELESS SIGNAL TRANSFERS BETWEEN ULTRASOUND-ENABLED MEDICAL DEVICES

CROSS-REFERENCE TO RELATED APPLICATION

This application claims priority under 35 U.S.C. §119 to U.S. Provisional Application No. 61/027,983, filed on Feb. 12, 2008, entitled "Systems and Methods for Controlling Wireless Signal Transfers Between Ultrasound-Enabled Medical Devices," which is incorporated herein by reference in its entirety.

TECHNICAL FIELD

The present invention relates to systems and methods for communicating between medical devices. More specifically, the present invention relates to systems and methods for controlling wireless signal transfers between ultrasound-enabled medical devices.

BACKGROUND

Implantable medical devices (IMDs) such as pacemakers and implantable cardioverter defibrillators are utilized in monitoring and regulating various conditions within the body. An implantable cardioverter defibrillator, for example, may be utilized in cardiac rhythm management applications to monitor the rate and rhythm of the heart and for delivering various therapies such as cardiac pacing, cardiac defibrillation, and/or cardiac therapy. In some cases, for example, the implantable medical device can be configured to sense various physiological parameters occurring in the atria and/or ventricles of the heart or at other locations to determine the occurrence of any abnormalities in the operation of the heart. Based on these sensed parameters, the medical device may then deliver an appropriate therapy to the patient.

A variety of techniques have been developed for transmitting wireless signals between medical devices located inside or outside of the body. In an ultrasonic approach, for example, each linked medical device can be equipped with an ultrasonic transducer adapted to generate an acoustic signal for providing data communications from one device to another device, to transfer energy from one device to another device, and/or to delivery therapy to a treatment site. One major obstacle limiting the advancement of the ultrasonic approach is the inefficiency of signal transfer from indirect acoustic pathways within the body between ultrasound-enabled devices. In a dynamic, heterogeneous environment such as the human body, for example, optimal signal transfer from one ultrasound-enabled device to another requires appropriately designed transmissions, typically in the form of modulated acoustic signals with compensations for phase and amplitude effects during propagation. Accordingly, there is an ongoing need for systems and methods for improving the accuracy, efficiency, and reliability of wireless signal transfers between ultrasound-enabled devices.

SUMMARY

The present invention relates to systems and methods for controlling wireless signal transfers between ultrasound-enabled medical devices. An illustrative system includes a source device with a plurality of acoustic transducer elements configured to transmit an acoustic signal, a target device including an acoustic transducer for receiving the acoustic signal from the source device, and a controller configured to determine adjustments to one or more transmission parameters of the source device for increasing the signal coherence at the target device. In some embodiments, the controller is configured to adjust the transmission parameters based on phase delay and/or amplitude differences from acoustic signals transmitted by the target device and received on the transducer elements of the source device.

An illustrative method for controlling the wireless transfer of acoustic signals between ultrasound-enabled medical devices includes initiating a transmission mode of operation in the target device and transmitting one or more acoustic signals from the target device, initiating a reception mode of operation in the source device and receiving one or more acoustic signals from the target device, comparing the acoustic signals received by a plurality of transducer elements of the source device and computing a phase delay parameter for the received acoustic signals, and adjusting one or more transmission parameters of the source device to increase the signal coherence at the target device.

The systems and methods described herein may enable optimal or near-optimal signal transfer over a wide range of operating conditions and in a variety of applications. Applications that can employ the techniques described herein can include, but are not limited to, telemetry communications, energy transfer or delivery, and therapy delivery. In some embodiments, for example, the techniques described herein can be utilized in cardiac rhythm management applications to control acoustic communications between an implantable pulse generator or an external monitoring device and a remote sensor implanted within the body. Other applications are also possible.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
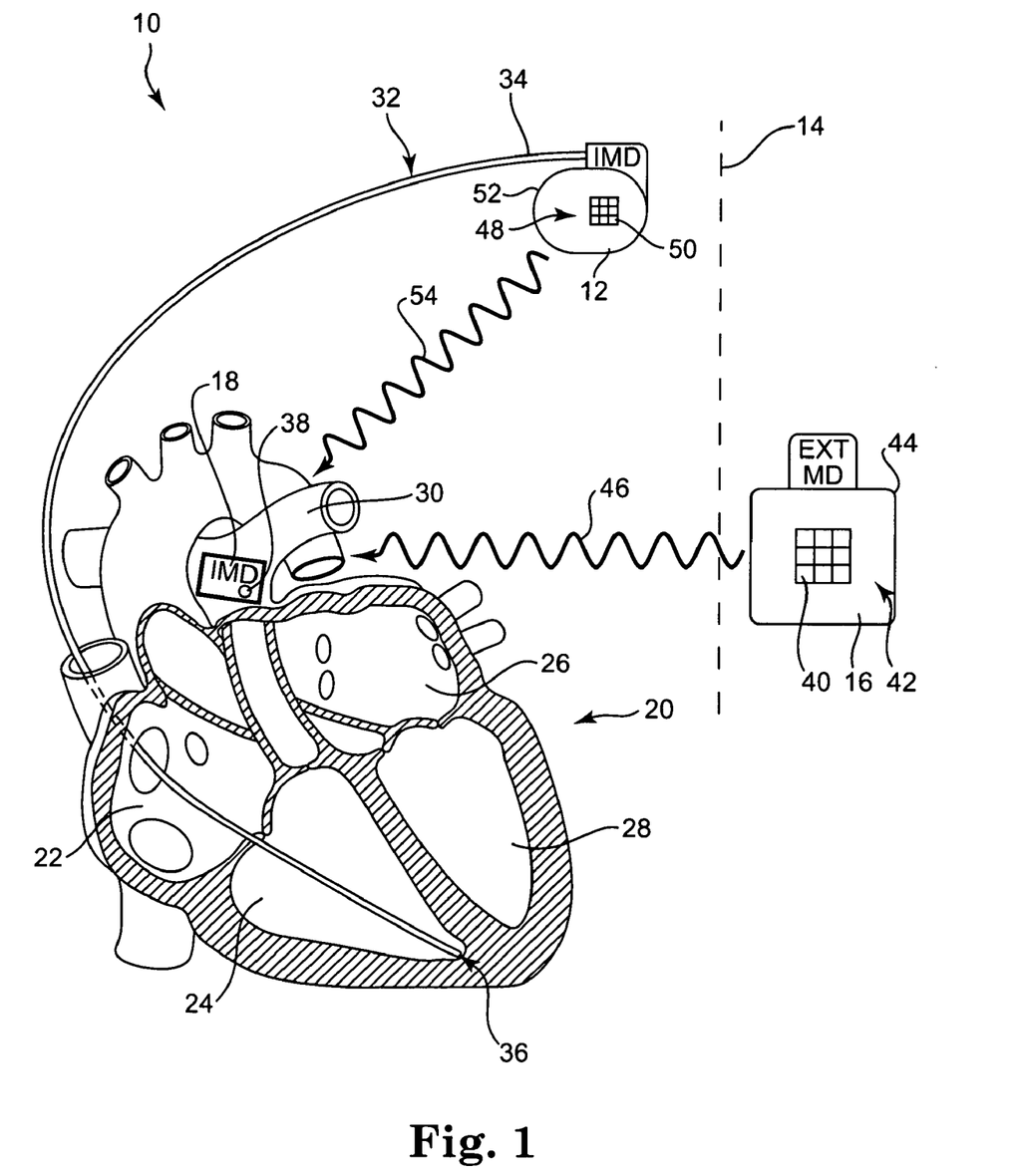
FIG. 1 is a schematic view showing an illustrative system for providing wireless transfer of acoustic signals between ultrasound-enabled medical devices.

FIG. 1 is a schematic view of an illustrative CRM system 10 for providing wireless transfer of acoustic signals between ultrasound-enabled medical devices implantable within a patient's body. The system 10, illustratively a system for optimizing the transfer of wireless signals in a cardiac rhythm management system, includes a medical device such as a pulse generator 12 implanted subcutaneously within the body at a location below the patient's skin 14, a monitor 16 located outside of the body, and a remote sensing device 18 implanted deeply within the patient's body (e.g., in one of the arteries or ventricles of the patient's heart 20 or in a pulmonary artery). The heart 20 includes a right atrium 22, a right ventricle 24, a left atrium 26, and a left ventricle 28. The right ventricle 24 leads to the main pulmonary artery 30, as shown.

In the illustrative CRM system 10 depicted, the pulse generator 12 is coupled to a lead 32 deployed in the patient's heart 20. As shown, the pulse generator 12 can be implanted subcutaneously within the body, typically at a location such as in the patient's chest or abdomen, although other implantation locations are possible. A proximal portion 34 of the lead 32 can be coupled to or formed integrally with the pulse generator 12. A distal portion 36 of the lead 32, in turn, can be implanted at a desired location within the heart 20 such as in the right ventricle 24, as shown. Although the illustrative system 10 depicts only a single lead 32 inserted into the patient's heart 20, in other embodiments the system 10 may include multiple leads so as to electrically stimulate other areas of the heart. 20. In some embodiments, for example, the distal portion of a second lead (not shown) may be implanted in the right atrium 22 or in the right ventricle 24. In addition, or in lieu, another lead can be implanted at the left side of the heart 20 (e.g., in the left atrium 26 or the left ventricle 28) to stimulate the left side of the heart 20, or can be implanted at other locations such as in the coronary veins (e.g., for biventricular pacing and/or heart failure treatment). Other types of leads such as epicardial leads may also be utilized in addition to, or in lieu of, the lead 32 depicted in FIG. 1.

During therapy, the lead 32 can be configured to convey electrical signals between the heart 20 and the pulse generator 12. For example, in those embodiments where the pulse generator 12 is a pacemaker, the lead 32 can be configured to deliver electrical therapeutic stimulus for pacing the heart 20. In those embodiments where the pulse generator 12 is an implantable cardiac defibrillator, the lead 32 can be utilized to delver electric shocks to the heart 20 in response to an event such as ventricular tachycardia. In some embodiments, the pulse generator 12 may include both pacing and defibrillation capabilities.

In the embodiment illustrated in FIG. 1, the monitor 16 is in acoustic communication with the remote sensing device 18 and the pulse generator 12. In certain embodiments, for example, the monitor 16 comprises an external device located on a handheld unit or on a garment adapted to be worn by the patient, and can be tasked to monitor the status of the patient's health as well as the operational and/or diagnostic status of the implanted devices 12,18. In certain embodiments, for example, the monitor 16 can be tasked to relay information about or acquired by the remote sensing device 18 to the pulse generator 12. Alternatively, and in other embodiments, the monitor 16 can be located within the patient's body. In certain embodiments, for example, the monitor 16 can be implanted subcutaneously within the body at a location adjacent to the pulse generator 12 or at some other desired location within the body.

The remote device 18 can be configured to perform one or more designated functions, including the sensing of physiological parameters within the body. Example physiological parameters that can be measured using the remote device 18 can include, but are not limited to, blood pressure, blood or fluid flow, temperature, and strain. Various electrical, chemical and/or magnetic properties may also be sensed within the body via the remote device 18. The specific configuration and function of the remote device 18 will typically vary depending on the particular diagnostic and therapeutic needs of the patient. In one illustrative embodiment, for example, the remote device 18 includes a pressure sensor that can be implanted at a location deep within the body such as the main pulmonary artery 30 or a branch of the main pulmonary artery 30 (e.g., in the right or left pulmonary artery). Alternatively, the remote device 18 can be implanted at other locations within the body, and can be configured to measure other parameters.

In use, the remote device 18 can be used as part of a system to predict decompensation of a heart failure patient or to optimize pacing and/or defibrillation therapy. The remote device 18 can be configured to transmit an acoustic data signal to the pulse generator 12, to the monitor 18, and/or to other medical devices located inside or outside of the body containing one or more physiological parameters sensed at the implantation location. Based on this information, an indication of any abnormalities within the heart 20 can be determined and an appropriate therapy provided to the patient, as necessary.

The remote device 18 can be tasked either alone or with other implantable devices to provide or regulate various therapies within the body. In certain embodiments, for example, the remote device 18 includes a glucose level sensor that can be used in conjunction with an insulin pump for providing insulin to the patient. In other embodiments, the remote device 18 can comprise a pulmonary sound sensor, a satellite pacing device, or other sensing and/or therapy-delivering device.

As further shown in FIG. 1, the remote device 18 can include an acoustic transducer 38 adapted to generate and receive acoustic waves for communication with, powering, and/or recharging the remote device 18 via an acoustic link. In certain embodiments, the acoustic transducer 38 is an ultrasound transducer having a resonant structure such as a flexible diagram. In other embodiments, however, the transducer may have a different configuration.

The monitor 16 includes multiple acoustic transducer elements 40, which as is discussed further herein, is configured to transmit and receive acoustic signals for establishing an acoustic link between the monitor 16 and the remote device 18, the pulse generator 12, and/or other medical devices inside or outside of the body. In some embodiments, for example, the monitor 16 includes a multi-element transducer (MET) array 42 coupled to a transducer housing 44. In the illustrative embodiment of FIG. 1, the MET array 42 is a two-dimensional array of ultrasonic transducer elements 40, although other configurations employing multiple transducer elements are also possible. In one alternative embodiment, for example, the MET array 42 comprises a three-dimensional array of transducer elements coupled to a spherically-shaped housing. In another alternative embodiment, the MET array 42 comprises a one-dimensional array of transducer elements.

The transducer elements 40 may operate at the same frequency, or alternatively, can operate at different frequencies. In one embodiment, for example, each of the transducer elements 40 are configured to operate at a frequency of between about 20 KHz and about 200 KHz. In some embodiments the transducer elements 40 may each operate at a frequency of about 40 KHz. The transducer elements 40 can be configured to resonate at the same frequency, or can be configured to resonate at different frequencies.

During operation, one or more of the transducer elements 40 can be actuated to produce an acoustic wave 46 that is used to establish an acoustic link between the monitor 16 and the remote device 18 for powering the remote device 18, for recharging the remote device 18, and/or for communicating sensor readings from the remote device 18. In some embodiments, the transducer elements 40 can also be used to establish an acoustic link between the monitor 16 and the pulse generator 12, if desired.

The phase delay, and in some cases also the amplitude, of the acoustic signals produced by each of the transducer elements 40 can be controlled by the monitor 16 in order to maximize the phase alignment of the acoustic wave 46 received at the remote device 18. The application of phase delays can be accomplished, for example, using a time-reversal technique with a cross-correlation algorithm that estimates the time-delay between signals from neighboring transducer elements, and then applies a time-reversing or phase-shifting of the signals provided to one or more of the transducer elements in order to align the phases of the acoustic signals received at the remote device 18. Such process of determining the cross-correlation of the signals received by the transducer elements and then applying phase delays to the transducer elements can be used to produce a coherent wave convergent at the remote device 18. This coherence of the acoustic wave can be accomplished, for example, by selecting an acoustic signal received at one transducer element for the monitor 16 as a reference signal and then adjusting the phase delays of the other transducer elements based on the reference signal to maximize the phase alignment of signals from all transducer elements. Alternatively, and in other embodiments, the coherence of the acoustic wave can be accomplished via a moving reference signal by comparing the phase delay for pairs of transducer elements, and then adjusting the phase delays on each of the transducer elements to maximize the phase alignment across all transducer elements.

In some embodiments, the process of analyzing the cross-correlation of the acoustic signals received on the transducer elements and then retransmitting the acoustic wave 46 with phase shifted compensation signals applied to one or more of the transducer elements can be performed iteratively, allowing the monitor 16 to continually or periodically adjust the phase attributes of the acoustic wave 46 in order to optimize the coherence of the acoustic wave 46 at the remote device 18.

In some embodiments, modulating the acoustic wave 46 can be conducted so as to improve the signal strength of the acoustic wave 46 received at the remote device transducer 38. In acoustic powering or recharging applications, for example, the increased signal strength of the acoustic wave 46 received at the transducer 38 increases the amount of electrical energy generated by the transducer 38 for powering the remote device 18 and/or for recharging a battery within the remote device 18. In communication applications, the increased signal strength of the acoustic wave 46 at the transducer 38 results in more accurate and efficient data transmissions back and forth between the remote device 18 and the monitor 16.

In the illustrative embodiment of FIG. 1, the pulse generator 12 further includes an array 48 of transducer elements 50 for establishing an acoustic link between the pulse generator 12 and the remote device 18. In some embodiments, for example, the pulse generator 12 includes a multi-element array 48 of transducer elements 50 coupled to a can 52 of the pulse generator 12, as shown. In use, the pulse generator 12 can be configured to transmit an acoustic wave 54 for communicating with the remote device 18 or for powering and/or recharging the remote device 18. In some embodiments, for example, the transducer elements 50 can be used to establish an acoustic link between the pulse generator 12 and the remote device 18 for sending an acoustic wake-up signal that prompts the remote device 18 to take one or more sensor readings within the body. When activated, the remote device 18 takes one or more sensor readings and transmits these readings back to the pulse generator 12 via the transducer 38, which can then used by the pulse generator 12 for providing therapy to the patient, if desired. As with the transducer elements 40 for the monitor 16, a time reversal technique may be used to maximize the phase alignment of the acoustic signals received at the remote device 18.

Figure 2:
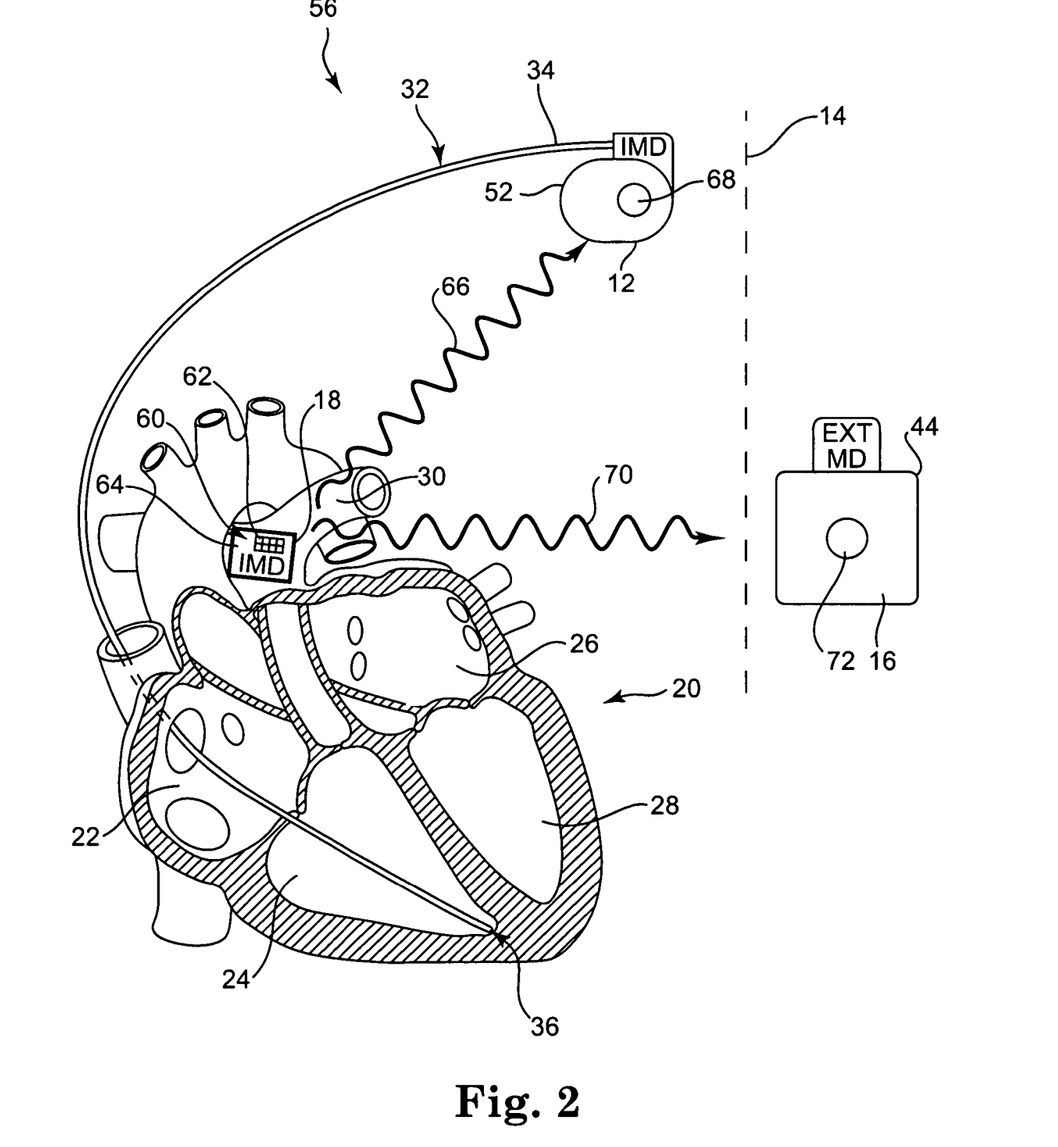
FIG. 2 is a schematic view showing another illustrative system for providing wireless transfer of acoustic signals between ultrasound-enabled medical devices.

FIG. 2 is a schematic diagram showing another illustrative CRM system 56 for providing wireless transfer of acoustic signals between ultrasound-enabled medical devices. In the illustrative system 56 of FIG. 2, the remote device 18 includes an array 60 of multiple transducer elements 62 configured to transmit and receive acoustic signals for establishing an acoustic link between the remote device 18 and the pulse generator 12, the monitor 16, and/or other medical devices in acoustic communication with the remote device 18. In some embodiments, for example, the remote device 18 includes a multiple element transducer (MET) array 60 coupled to a transducer housing 64 of the remote device 18, although other configurations are possible.

During operation, one or more of the transducer elements 62 can be actuated to produce an acoustic wave 66 that can be received by an acoustic transducer 68 of the pulse generator 12. In some embodiments, and as further shown in FIG. 2, the transducer elements 62 can also be actuated to produce an acoustic wave 70 that is received by an acoustic transducer 72 of the monitor 16. The phase delay of the acoustic signals produced by each of the transducer elements 62 can be controlled by the remote device 18 in order to maximize the phase alignment of the acoustic waves 66,70. For example, the phase delay of the acoustic signals generated by the transducer elements 62 can be controlled in order increase the signal strength of the acoustic waves 66,70 received by the pulse generator 12 and the monitor 16.

In some embodiments, the remote device 18 is configured to transmit a single acoustic wave that can be received by both the pulse generator 12 and the monitor 16. As with those embodiments in which a separate acoustic wave 66,70 is transmitted to each device 12,16 in communication with the remote device 18, the single acoustic wave generated can be modulated to improve signal coherence at each of the communicating devices 12,16, thereby optimizing the signal strength of the acoustic wave received by each device 12,16.

Figure 3:
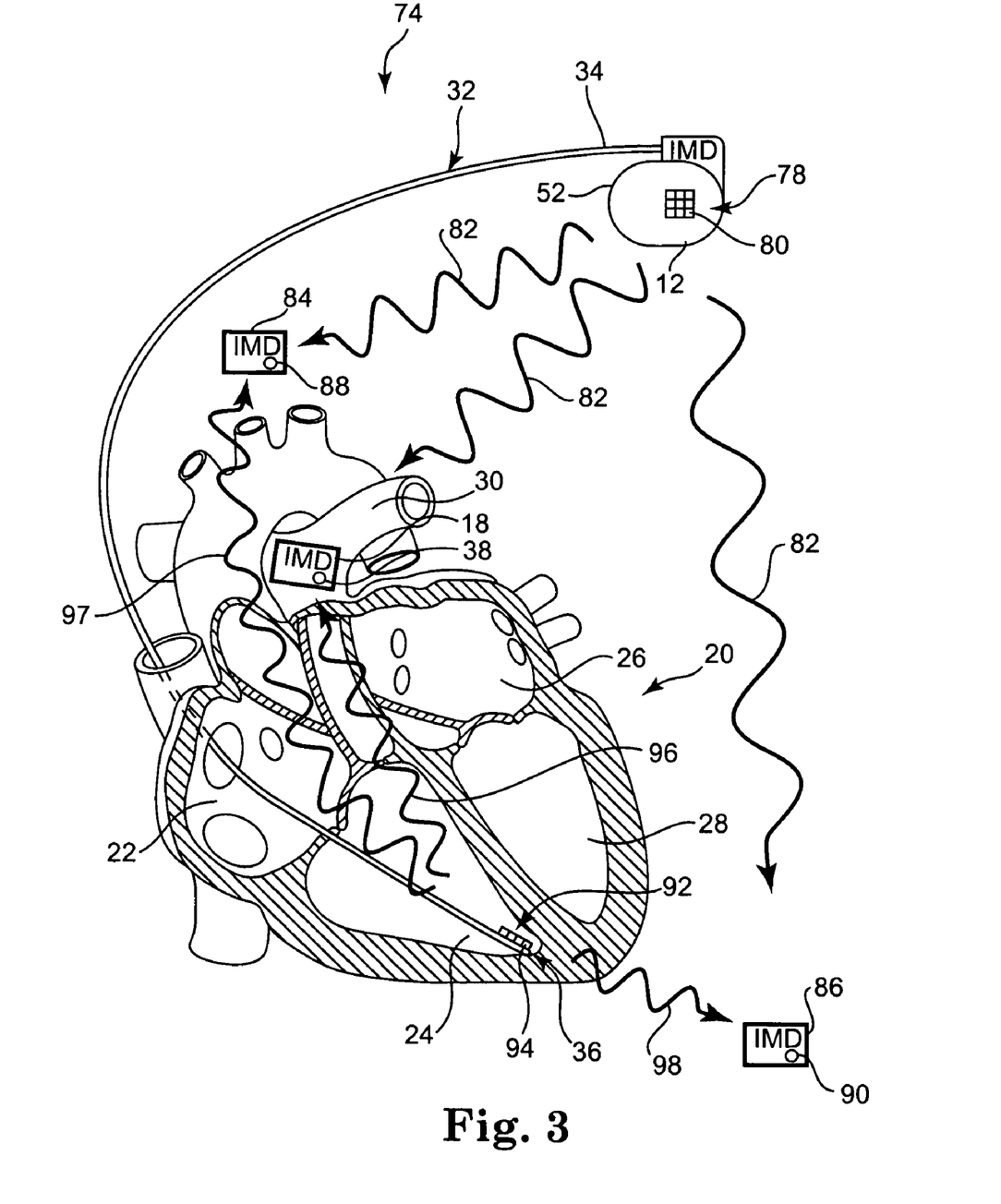
FIG. 3 is a schematic view showing another illustrative system for providing wireless transfer of acoustic signals between ultrasound-enabled medical devices.

FIG. 3 is a schematic view showing another illustrative CRM system 74 for providing wireless transfer of acoustic signals between ultrasound-enabled medical devices. In the illustrative system 74 of FIG. 3, a pulse generator 12 equipped with a first array 78 of transducer elements 80 is configured to transmit an acoustic wave 82 that can be received by multiple medical devices 18,84,86 implanted within the body. Each implanted medical device 18,84,86 can be equipped with a transducer element 38,88,90 configured to receive, and in some embodiments also transmit, acoustic waves.

In some embodiments, the acoustic wave 82 generated by the transducer elements 80 can be modulated to improve signal coherence across each of the communicating devices 18,84,86. For example, the acoustic wave 82 generated by the pulse generator 12 can be configured to produce a coherent acoustic wave 82 in order to optimize the signal strength of the acoustic wave 82 received by each of the communicating devices 18,84,86. In other embodiments, the acoustic wave 82 generated by the pulse generator 12 can be configured to optimize the signal strength at one of the implanted medical devices (e.g., the remote sensing device 18) while also permitting communications with one or more of the other implanted medical devices. Other configurations, however, are possible.

The CRM system 74 further includes a second array 92 of transducer elements 94 configured to transmit one or more acoustic waves 96,97,98 within the body that can be received by one or more of the implanted medical devices 18,84,86. In some embodiments, for example, the second array 92 of transducer elements 94 is configured to direct a first acoustic wave 96 that can be received by the remote device 18, a second acoustic wave 97 that can be received by another device 84 implanted within the body, and a third acoustic wave 98 that can be received by yet another device 86 implanted within the body. In the illustrative embodiment of FIG. 3, the second array 92 of transducer elements 94 is coupled to the distal portion 36 of the lead 32. In other embodiments, the transducer array 92 can be coupled to other sections of the lead 32, to other leads coupled to the pulse generator 12, or to other portions of the pulse generator 12. In some embodiments, the transducer array 92 can be coupled to other devices or structure located within the body such as a sensor or therapy delivery device.

As with other embodiments described herein, the phase delay, and in some cases also the amplitude, of the acoustic signals produced by each of the second array 92 of transducer elements 94 can be controlled in order to modulate the acoustic waves 96,97,98 within the body. In some embodiments, for example, the modulation of the acoustic waves 96,97,98 can be accomplished using a time-reversal technique to improve the signal strength of the waves 96,97,98 received at the transducers 38,88,90 for each device 18,84,86.

Figure 4:
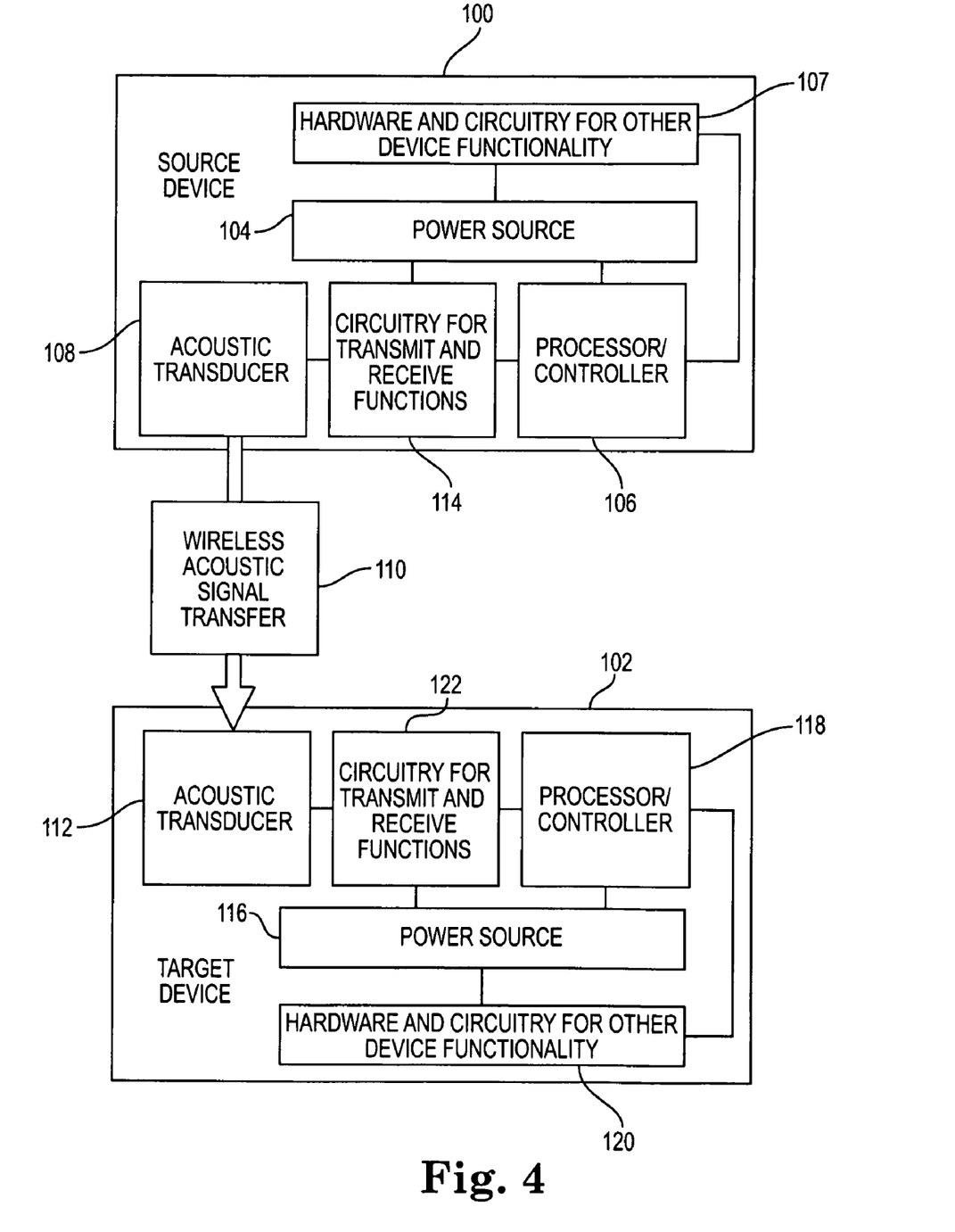
FIG. 4 is a block diagram showing several illustrative components of a source device in acoustic communication with a target device.

FIG. 4 is a block diagram showing several illustrative components of a source device 100 acoustically coupled with a target device 102. The source device 100, which can comprise a pulse generator or external monitor similar to that described above, for example, with respect to FIG. 1, includes a power source 104 for powering the device 100, and a processor/controller 106 for controlling the operation of the device 100 including various hardware and circuitry 107 within the device 100. In those embodiments in which the source device 100 is a pulse generator, for example, the processor/controller 106 can be configured to control the hardware and circuitry 107 in order to deliver electrical therapy stimulus or pacing signals to the patient via a lead or multiple leads.

In the illustrative embodiment of FIG. 4, the source device 100 further includes an acoustic transducer 108 for transmitting an acoustic wave 110 between the source device 100 and the target device 102. The acoustic transducer 108 includes multiple transducer elements, each of which can be controlled by the processor/controller 106 to steer, shape, focus, and/or otherwise modulate the acoustic wave 110 to improve signal coherence at an acoustic transducer 112 for the target device 102. In certain embodiments, for example, the processor/controller 106 is configured to modulate the acoustic wave 110 using a time-reversal technique to improve the efficiency of acoustic energy transmitted to the target device 102 for acoustically powering and/or recharging the device 102. In other embodiments, the processor/controller 106 is configured to modulate the acoustic wave 110 using a time-reversal technique to improve the efficiency of wireless communications between the source device 100 and the target device 102. In other embodiments, the processor/controller 106 is configured to modulate the acoustic wave 110 using a time-reversal technique to improve the efficiency of acoustic energy transmitted to the target device 102 for providing therapy to a treatment site within the body.

In some embodiments, the source device 100 further includes circuitry 114 that permits the acoustic transducer 108 to operate in both a transmit mode and a receiving mode, allowing the transducer 108 to further receive acoustic signals from the target device 102 and/or other medical devices in communication with the source device 100. In other embodiments, the source device includes separate transducers for transmitting and receiving acoustic signals.

The target device 102 includes a power source 116 for powering the device 102, and a processor/controller 118 for controlling the operation of the device 102 including various hardware and circuitry 120 within the device 102. In those embodiments in which the target device 102 comprises a remote sensor such as a pressure sensor, for example, the processor/controller 118 can be configured to control the hardware and circuitry 120 to sense pressure readings within the body and then transmit those readings as an acoustic signal via the acoustic transducer 112.

The acoustic transducer 112 for the target device 102 includes one or more acoustic transducer elements configured to receive the acoustic wave 110 transmitted by the source device 100, and then convert those signals into electrical signals for further processing by the processor/controller 118. In some embodiments, the acoustic transducer 112 comprises a single transducer element adapted to receive the acoustic wave 110. In other embodiments, the acoustic transducer 112 comprises multiple transducer elements and/or an array of transducer elements. In certain embodiments, the target device 102 further includes circuitry 122 that permits the acoustic transducer 112 to operate in both a transmit mode and a receiving mode, allowing the transducer 112 to further transmit acoustic signals to the source device 100 or other medical devices. In other embodiments, the source device includes separate transducers for transmitting and receiving acoustic signals.

Figure 5:
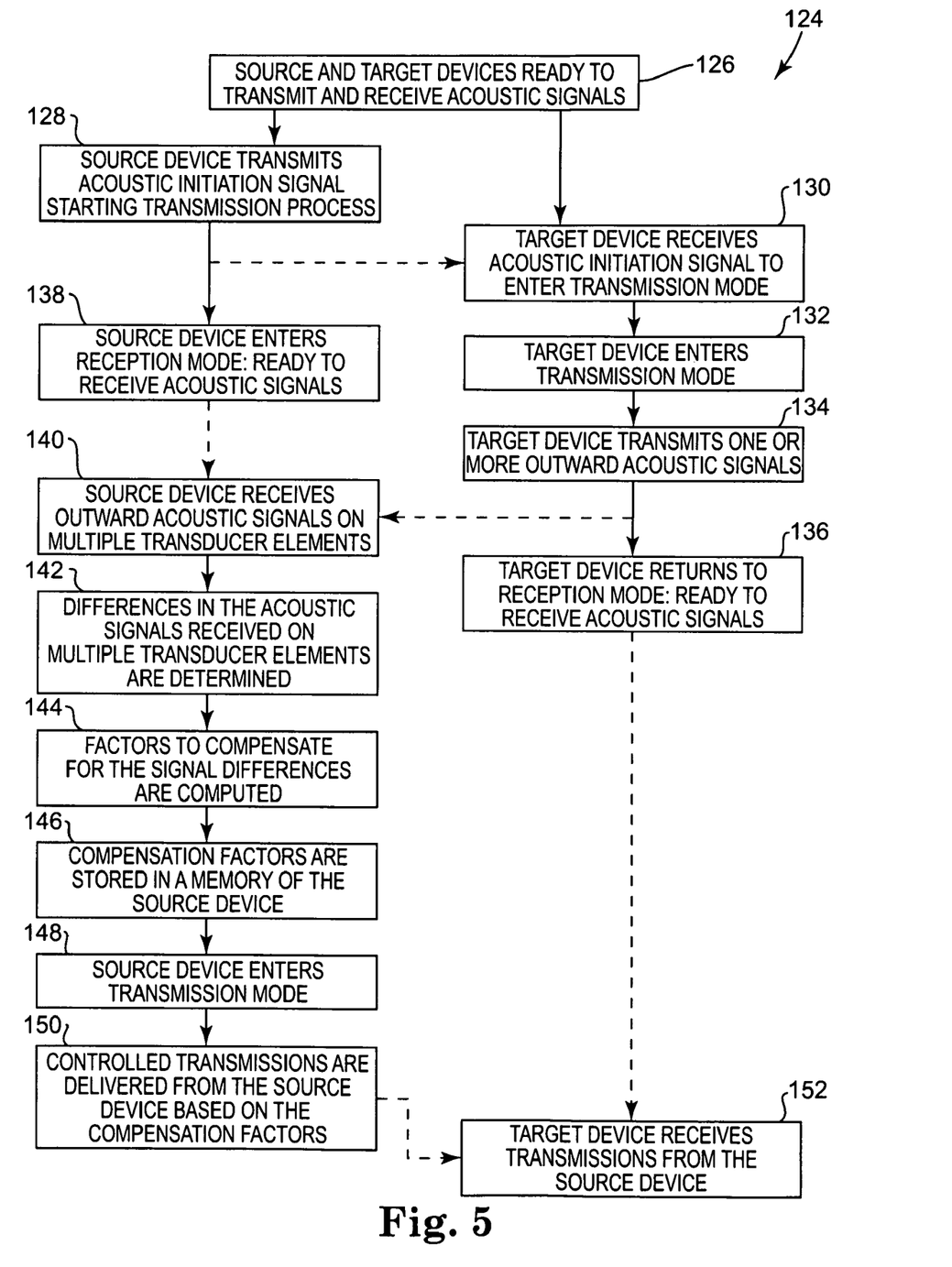
FIG. 5 is a flow chart showing an illustrative method for controlling the wireless transfer of acoustic signals between ultrasound-enabled medical devices.

FIG. 5 is a flow chart showing an illustrative method 124 for controlling the wireless transfer of acoustic signals between ultrasound-enabled medical devices. The method 124 begins generally at block 126 with a source device and target device ready to transmit and receive acoustic signals. The source device and target device may comprise, for example, the source device 100 and target device 102 described above in FIG. 4, although other configurations are possible.

Once configured, the source device may transmit an acoustic initiation signal to the target device (block 128). The acoustic initiation signal may comprise, for example, a series of pulses spaced apart by a predetermined period of time, or a single acoustic pulse having a particular characteristic (e.g., amplitude, frequency, duration, etc.) that can be recognized by the target device as a request to initiate communications with the target device. In certain embodiments, the acoustic initiation signal may comprise a first acoustic pulse followed by a second acoustic pulse spaced apart from the first acoustic pulse by a predetermined period of time (e.g., 1 second). In some embodiments, the acoustic initiation signal can be transmitted to the target device from another medical device located inside or outside of the patient's body. In certain embodiments, the acoustic initiation signal may comprise a signal other than an acoustic signal such as an RF or inductive signal transmitted to the target device from another medical device located inside or outside of the patient's body. In other embodiments, initiation of the target device into a transmission mode of operation can be accomplished via an internal clock or timer signal within the target device.

Upon receiving the initiation signal transmitted by the source device (130), the target device enters into a transmission mode of operation (block 132). In this mode, the target device acts as a beacon, transmitting a number of outward acoustic signals (block 134). The acoustic signals transmitted by the target device can have a predetermined amplitude and duration, or alternatively, can be pulses representing a unique device identification and/or a measured value. In some embodiments, for example, the target device is configured to transmit an acoustic pulse train that is used by the source device to uniquely identify the target device from other devices implanted within the body. Once the target device has transmitted one or more acoustic signals (block 134), the target device may then return to a reception mode of operation to receive acoustic signals from the source device (block 136).

The source device is configured to enter into a reception mode of operation for receiving the acoustic signals transmitted from the target device (block 138). The acoustic signals transmitted from the target device are then received on each element of the multiple element transducer of the source device (block 140). Circuitry within the source device then converts each acoustic signal into corresponding electrical signals.

The processor/controller for the source device receives the electrical signals for each transducer element and then compares the differences in each signal (block 142). In some embodiments, for example, the processor/controller is configured to compute a phase delay parameter and, in some cases also an amplitude parameter, corresponding to each transducer element. From these computed phase delay and/or amplitude parameters, the processor/controller computes one or more compensation factors to adjust the characteristics of the acoustic signal transmitted from the source device to the target device (block 144). In some embodiments, the processor/controller is configured to compute a phase delay parameter to be applied to one or more of the transducer elements in order to maximize the phase alignment of the acoustic signals received at the acoustic transducer for target device. Computing of the phase delay compensation parameters can be accomplished, for example, using a time-reversal technique with a cross-correlation algorithm that estimates the time delays between signals received on neighboring transducer elements and then applies a phase shifting of the signals provided to one or more of the transducer elements based on these time-delay estimates. The computed compensation factors to be applied for each transducer element 50 are then stored within a storage memory of the source device (block 146).

The compensation factors determined for each transducer element can be obtained sequentially or simultaneously. In a sequential approach, the compensations factors can be determined one at a time, requiring multiple transmissions from the target device. In a simultaneous approach, in contrast, the compensation factors can be determined all at once from a single acoustic transmission from the target device. The process of computing phase delay parameters to be applied to the transducer elements can be performed iteratively in some embodiments. For example, the phase delay parameters can be continuously or periodically updated over time, allowing the system to dynamically compensate for any changes in movement of the target and/or source devices (e.g., due to movement from the cardiac or respiratory rhythms or a change in body position).

Once the compensation factors are computed and stored in memory, the source device enters into a transmission mode of operation (block 148) and controls the transmission of acoustic signals to the target device based at least in part on the computed phase delay and/or amplitude compensation factors (block 150). The adjustments to the transmission parameters can include the use of multiple sets of temporally-dependent or event-dependent adjustments. In some embodiments, for example, the processor/controller can be configured to control the transmission of the acoustic signals over a particular time period or based on the occurrence of a particular event such as the detection of patient movement or a change in body position from an accelerometer or other motion sensing device.

With the compensation factors applied to the source device transducer elements, the target device then receives the compensated acoustic signals transmitted by the source device (block 152). The process of iteratively updating the phase delay compensation parameters applied to the transducer elements can be repeated continuously, at predetermined time periods (e.g., once every 5 minutes), or upon the detection of an event (e.g., upon the detection of movement or orientation of the patient).

Based on these compensated factors, the acoustic signals can be transmitted optimally through a complicated path or between unaligned source and target devices in the presence of organs and other obstructions located within the body. In some embodiments, for example, the processor/controller for the source device may apply reverse or time-shifted delays to one or more of the source device transducer elements to produce a coherent acoustic wave at the target device.

The compensation factors can be obtained for both programmed and dynamic tracking use scenarios. If the source device and target device are relatively stationary, a single set of compensation factors can be determined, stored in memory, and then applied successively for future transmissions. If, for example, the source device and target device move cyclically (e.g., in response to cardiac or respiratory rhythms), compensation factors at different portions of the cycle can be computed and utilized. If the source device and target device move within a fixed range, compensation factors at the extremes (e.g., towards the outer periphery of the transducer elements of a transducer array) can be determined and used to create a central average. The compensation factors can be obtained on-demand, prior to each signal transfer session, periodically, or according to changes in an auxiliary signal such as a heart rate signal or a respiration rate signal.

In some embodiments, the processor/controller for the source device can be configured to operate all of the transducer elements simultaneously. In another embodiment, the processor/controller for the source device may determine which transducer element or elements have a low attenuation in the acoustic path to the target device and operate only those transducer elements.

The ability to dynamically modulate the acoustic wave by modification of the phase delay and/or amplitude parameters applied to the transducer elements may increase the efficiency in amplitude-dependent applications such as energy transfer and energy delivery. For acoustic charging applications, for example, the modified acoustic wave may increase the efficiency of the energy transfer and reduce the potential for interruptions due to cardiac or respiratory rhythm induced movement of the target device. In some cases, the ability to modulate the acoustic wave may increase usability of the source device by reducing or eliminating the need to place the device at a precise location in the patient's body, enabling use of the device in a variety of different positions and orientations. The ability to modulate the acoustic wave can also increase the accuracy in signal-to-noise dependent applications such as during data transmissions and communications by reducing energy loss within the body.

The modified acoustic wave generated by the source device transducer elements can be utilized to optimize or near-optimize the transfer of acoustic signals to the target device and perform communications, energy delivery, therapy, or other desired functions within the body. In some embodiments, for example, the modified acoustic wave can be used to optimize the wireless transfer of communications back and forth between the target device and the source device. In addition, in some embodiments the modified acoustic wave can be used to acoustically recharge a battery, power capacitor or other such energy source within the target device. In other embodiments, the modified acoustic wave can be utilized by the target device to provide therapy to one or more treatment sites within the body. In still other embodiments, the acoustic wave produced is configured to create controlled cell and tissue ablation or to induce beneficial biological responses or effects such as thrombi dissolution or tissue stimulation.

Figure 6:
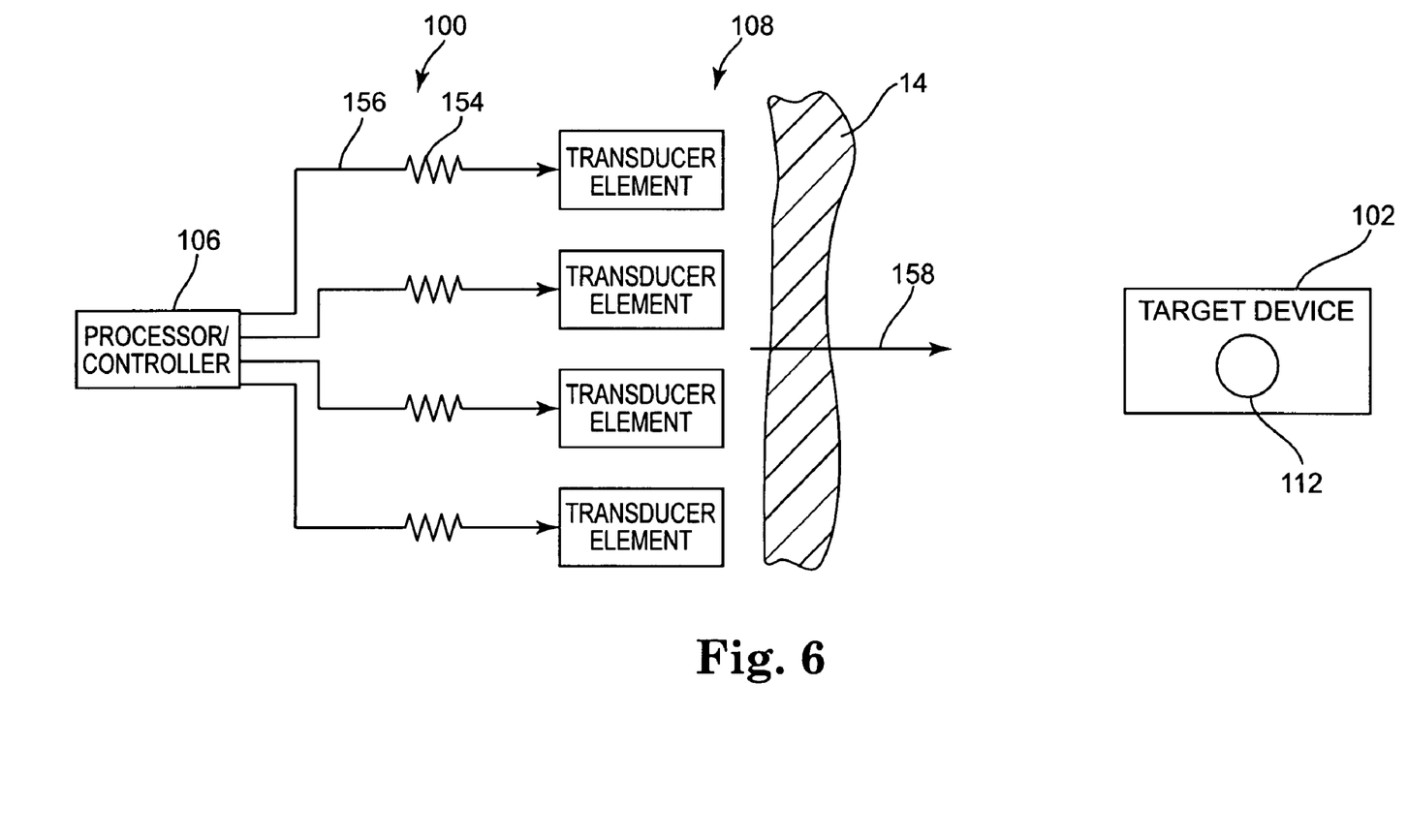
FIGS. 6-8 are schematic views showing an illustrative implementation of the method of FIG. 5 using an extracorporeal source device attached to the exterior surface of a patient's body.
Figure 7:
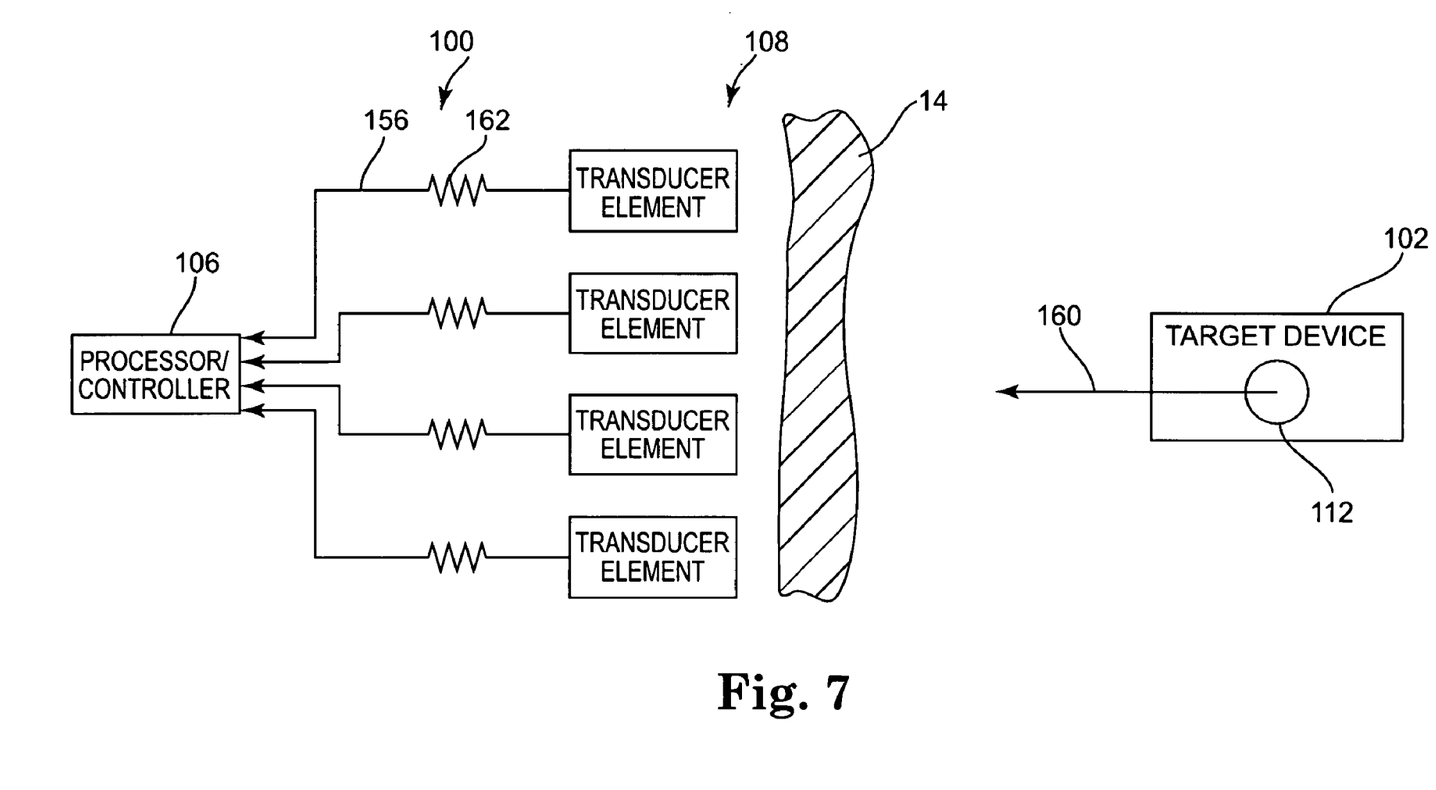
Figure 8:
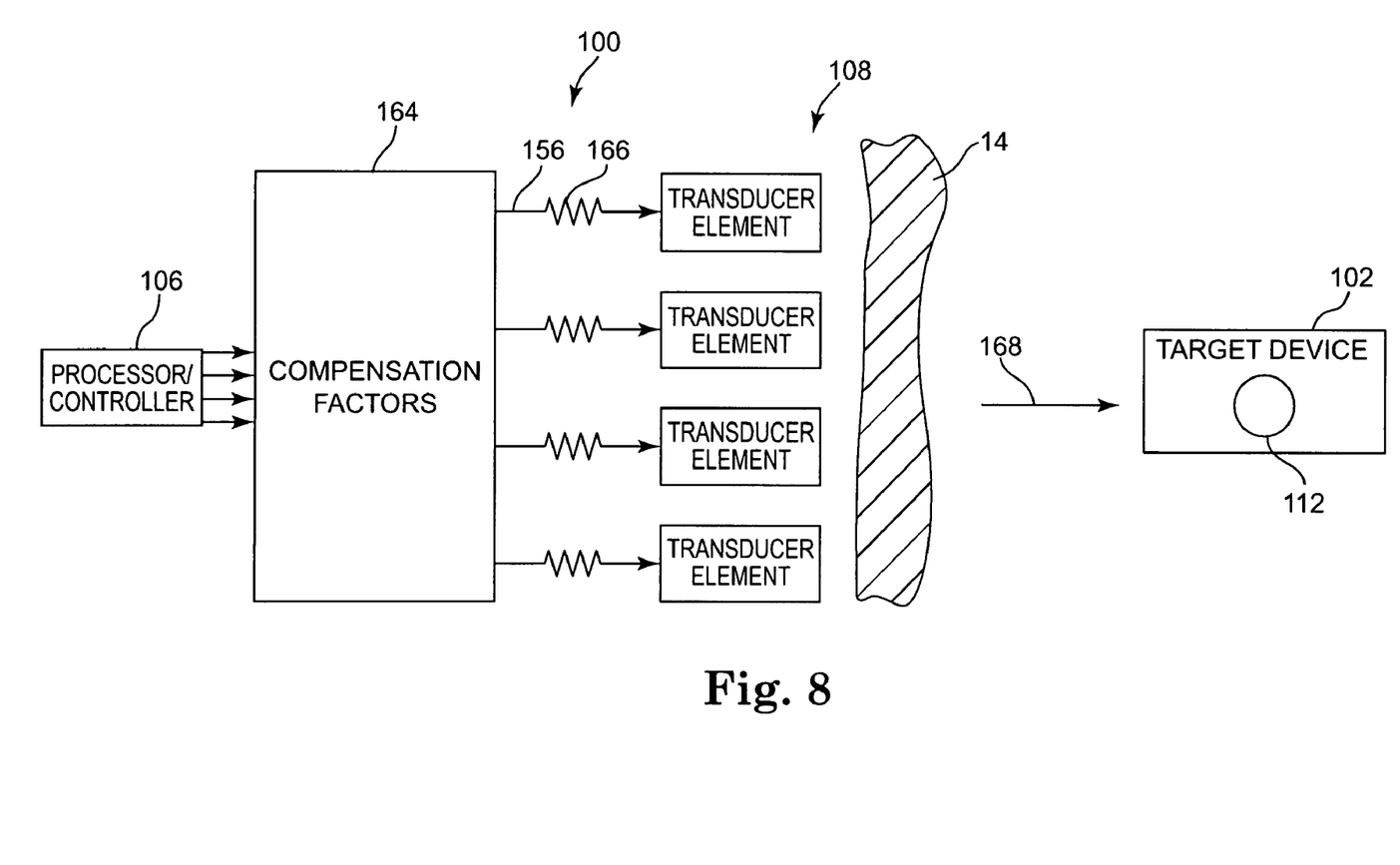

FIGS. 6-8 are schematic views showing an illustrative implementation of the method of FIG. 5 using an extracorporeal source device 100 attached adjacent to the exterior surface 14 of a patient's body. As shown in a first view in FIG. 6, the processor/controller 106 can be configured to transmit an electrical signal 154 on a separate channel 156 of each transducer element, initially producing an outward acoustic wave 158 through the surface 14 and into the patient's body towards the general direction of the target device 102.

Upon receiving the acoustic wave 158, the target device 102 can be configured to enter into a transmission mode of operation. In this mode, and as further shown in FIG. 7, the target device 102 transmits one or more acoustic pulses 160 to the source device 100. In certain embodiments, for example, the target device 102 transmits an acoustic pulse train that can be used to uniquely identify the target device 102 from any other devices implanted within the body.

The acoustic transducer 108 for the source device 100 is configured to convert the acoustic signals received at each transducer element into a corresponding electrical signal 162. The electrical signals 162 for each channel 156 are fed to the processor/controller 106, which computes phase delay parameters, and in some cases also amplitude parameters, to be applied to one or more of the transducer elements.

Based at least in part on the computed phase delay and/or amplitude factors, the processor/controller 106 may then apply compensation factors to one or more of the transducer elements during transmission of an acoustic wave towards the target device. As can be further seen in FIG. 8, for example, the processor/controller 106 can be configured to apply compensation factors 164 to produce electrical signals 166 for time delaying and/or adjusting the amplitude of the acoustic signals outputted by one or more of the transducer elements. As indicated generally by arrow 168, these compensated electrical signals 166 produce a coherent acoustic wave at the target device 102 despite a complex path of organs and other obstructions within the body and misalignment between the target device 102 and the source device 100. The compensated acoustic wave 168 transmitted by the source device 100 can then be used by the target device 102 for charging a rechargeable battery or power capacitor, to provide a communications link between the target device and the source device 100, for delivering therapy to targeted locations of the body, and/or for performing some other desired function within the body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for controlling the wireless transfer of acoustic signals between ultrasound-enabled medical devices, the method comprising:
   providing a source device equipped with a plurality of acoustic transducer elements configured to transmit and receive an acoustic signal;
   providing a target device equipped with at least one acoustic transducer element configured to receive acoustic signals transmitted from the source device and transmit acoustic signals to the source device;
   entering the target device into a transmission mode of operation and transmitting one or more acoustic signals from the target device;
   entering the source device into a reception mode of operation and receiving the one or more acoustic signals from the target device on the transducer elements of the source device;
   iteratively comparing the acoustic signals received by the source device transducer elements against a reference signal, performing a cross-correlation of the acoustic signals received by the source device transducer elements from the target device, and computing a phase-delay parameter for each transducer element; and
   dynamically adjusting one or more transmission parameters of the source device to increase the signal coherence at the target device over time, the transmission parameters including at least one temporally-dependent or event-dependent adjustment, wherein adjusting the one or more transmission parameters of the source device includes computing, based on one or more of the computed phase-delay parameters, at least one compensation factor for adjusting at least one characteristic of an acoustic signal transmitted from one or more of the transducer elements of the source device.

2. The method of claim 1, wherein comparing the acoustic signals received by the source device transducer elements further includes computing an amplitude parameter for one or more transducer elements.

3. The method of claim 1, wherein the at least one compensation factor includes at least one phase delay compensation factor.

4. The method of claim 1, wherein the at least one compensation factor includes at least one amplitude compensation factor.

5. The method of claim 1, wherein the at least one compensation factor includes a plurality of compensation factors, wherein the plurality of compensation factors are computed simultaneously based on a single acoustic signal received from the target device.

6. The method of claim 1, wherein at least one compensation factor includes a plurality of compensation factors, wherein the plurality of compensation factors are computed sequentially based on multiple acoustic signals received from the target device.

7. The method of claim 1, wherein adjusting one or more transmission parameters of the source device is accomplished using multiple sets of temporally-dependent adjustments.

8. The method of claim 1, wherein adjusting one or more transmission parameters of the source device is accomplished using multiple sets of event-dependent adjustments.

9. The method of claim 1, wherein entering the target device into a transmission mode of operation is accomplished via an acoustic initiation signal from the source device.

10. The method of claim 1, wherein entering the target device into a transmission mode of operation is accomplished via an acoustic or electromagnetic initiation signal from a device other than the source device.

11. The method of claim 1, wherein entering the target device into a transmission mode of operation is accomplished via an internal clock or timer signal within the target device.

12. A method for controlling the wireless transfer of acoustic signals between ultrasound-enabled medical devices, the method comprising:
   providing a source device including a plurality of acoustic transducer elements configured to transmit and receive an acoustic signal;
   providing a plurality of target devices each equipped with at least one acoustic transducer configured to receive acoustic signals transmitted from the source device and to transmit acoustic signals to the source device;
   entering each of the target devices into a transmission mode of operation and transmitting one or more acoustic signals using each target device;
   entering the source device into a reception mode of operation and receiving the one or more acoustic signals from each target device using the plurality of transducer elements of the source device;
   comparing the acoustic signals received by the source device transducer elements and computing a phase-delay parameter for each transducer element;
   computing, based on at least one of the computed phase-delay parameters, at least one compensation factor for adjusting at least one characteristic of an acoustic signal transmitted from one or more of the source device transducer elements; and
   adjusting one or more transmission parameters of the source device to increase the signal coherence of acoustic signals received by each target device from the source device, wherein adjusting the one or more transmission parameters includes applying the at least one compensation factor to the one or more of the source device transducer elements.

13. A system for controlling the wireless transfer of acoustic signals between ultrasound-enabled medical devices, the system comprising:
   a source device including a plurality of acoustic transducer elements;
   a target device including an acoustic transducer;
   a controller configured to determine adjustments to one or more transmission parameters of the source device to increase signal coherence at the target device; and
   wherein the controller is configured to dynamically adjust the one or more transmission parameters based at least in part on one or more compensation factors computed based on a cross-correlation of phase delay differences from acoustic signals transmitted by the target device and received at one or more of the transducer elements of the source device over time, the one or more transmission parameters including at least one temporally-dependent or event-dependent adjustment.

14. The system of claim 13, wherein both the source device and the target device are implantable medical devices.

15. The system of claim 13, wherein either the source device or the target device is an implantable medical device.

16. The system of claim 13, wherein the plurality of acoustic transducer elements includes an array of ultrasonic transducer elements.

17. The system of claim 13, wherein the plurality of acoustic transducer elements includes multiple ultrasonic transducer devices.

18. The system of claim 13, wherein the acoustic transducer of the target device is a single acoustic transducer.

19. The system of claim 13, wherein the controller includes one or more sets of compensation factors for adjusting the transmission of acoustic signals from the source device.

* * * * *